US012728093B2

(12) United States Patent
Fuhrmann et al.

(10) Patent No.: US 12,728,093 B2
(45) Date of Patent: Sep. 8, 2026

(54) OROMUCOSAL THERAPEUTIC SYSTEM CONTAINING AN ADHESIVE LAYER

(71) Applicant: LTS LOHMANN THERAPIE-SYSTEME AG, Andernach (DE)

(72) Inventors: Marlene Fuhrmann, Kail (DE); Marius Bauer, Andernach (DE)

(73) Assignee: LTS LOHMANN THERAPIE-SYSTEME AG, Andernach (DE)

(*) Notice: Subject to any disclaimer, the term of this patent is extended or adjusted under 35 U.S.C. 154(b) by 196 days.

(21) Appl. No.: 18/844,512

(22) PCT Filed: Mar. 8, 2023

(86) PCT No.: PCT/EP2023/055946
§ 371 (c)(1),
(2) Date: Sep. 6, 2024

(87) PCT Pub. No.: WO2023/170185
PCT Pub. Date: Sep. 14, 2023

(65) Prior Publication Data

US 2025/0228769 A1 Jul. 17, 2025

(30) Foreign Application Priority Data

Mar. 11, 2022 (EP) .................................... 22161726

(51) Int. Cl.
*A61K 9/00* (2006.01)
*A61K 47/02* (2006.01)
*A61K 47/20* (2006.01)
*A61K 47/32* (2006.01)
*A61K 47/36* (2006.01)

(52) U.S. Cl.
CPC .............. *A61K 9/006* (2013.01); *A61K 47/02* (2013.01); *A61K 47/20* (2013.01); *A61K 47/32* (2013.01); *A61K 47/36* (2013.01)

(58) Field of Classification Search
CPC ........ A61K 9/006; A61K 47/02; A61K 47/20; A61K 47/32; A61K 47/36
See application file for complete search history.

(56) References Cited

U.S. PATENT DOCUMENTS 6,562,363 B1 5/2003 Mantelle
2024/0216299 A1 7/2024 Mohr

FOREIGN PATENT DOCUMENTS

KR 100794264 B1 1/2008
WO WO-2020260725 A1 12/2020

OTHER PUBLICATIONS

International Search Report and Written Opinion for Application No. PCT/EP2023/055946, European Patent Office, Netherlands, mailed on May 9, 2023, 10 pages.

*Primary Examiner* — Trevor Love
(74) *Attorney, Agent, or Firm* — Sterne, Kessler, Goldstein & Fox P.L.L.C.

(57) ABSTRACT

The present invention relates to oromucosal therapeutic systems comprising a backing layer, an adhesive layer, and an active agent-containing layer, such oromucosal therapeutic systems for use in a method of treatment and/or prophylaxis, processes of manufacture of such oromucosal therapeutic systems as well as adhesive layers and bi-layer laminates for such oromucosal therapeutic systems.

17 Claims, No Drawings

OROMUCOSAL THERAPEUTIC SYSTEM CONTAINING AN ADHESIVE LAYER

TECHNICAL FIELD OF THE INVENTION

The present invention relates to an oromucosal therapeutic system comprising a backing layer, an adhesive layer and an active agent-containing layer with a relatively long retention time in the oral cavity, and adhesive layers and bi-layer laminates for such systems as well as processes of manufacture and uses thereof in medicinal treatment or prophylaxis.

BACKGROUND OF THE INVENTION

Medicaments are most often given in the form of oral solid or liquid dosage forms such as tablets, capsules, granules or syrups, which are easy and convenient to take and allow self-administration. However, these types of dosage forms have the disadvantage that the drug is absorbed via the gastrointestinal (GI) tract and that the bioavailability is often greatly reduced due to being metabolized before reaching the systemic circulation (so-called first-pass effect).

The oral mucosa is an administration site that is not yet as much used as traditional oral dosage forms but offers the advantage of combining the ease and convenience of use with bypassing the GI-tract, since the drug is absorbed into the systemic circulation directly via the mucosal tissue.

Oromucosal therapeutic systems, or oromucosal delivery systems (sometimes also termed buccal patches, oromucosal films, etc.), consist of one or more thin layers which are applied and adhere to the mucosa of the oral cavity to deliver the drug over a period of time. Dosage forms in the form of thin films for application in the oral cavity are also sometimes referred to as "Oral Thin Film" or OTF, however, many OTFs are not intended to adhere to the mucosa. In an oromucosal therapeutic system, the active is typically contained in a dissolvable or erodible layer, which often has mucoadhesive properties. As the film adheres to the mucosa, delivery of the active ingredient may be achieved by a combination of direct active release from the oromucosal therapeutic system to the mucosa, and, in the absence of a backing layer, by an indirect delivery of the active via dissolution in the saliva, often followed by swallowing of the saliva and absorption of the active ingredient from the gastrointestinal tract. In order to prevent the indirect active delivery inherent to open systems, a backing layer may be employed, which serves to shield the active-containing layer from the remaining parts of the oral cavity, in particular from the saliva of the environment. Ideally, OTFs do not provoke any negative sensation of having a disturbing object in the mouth, since the film, adhered to the mucosa, does not freely move around in the oral cavity, and since the film is usually thin enough not to be perceived by the patient once applied.

However, oromucosal therapeutic systems are a relatively new form of drug delivery, meaning that knowledge on formulation technology is limited. Formulating appropriate dosage forms for the oromucosal delivery by OTFs is challenging due to a multitude of aspects to be considered and issues to be solved.

One such aspect is the intended retention time in the oral cavity. While the mucosa is, e.g., compared to the skin, highly permeable and many actives are rapidly absorbed so that there is no need for the film to adhere to the mucosa for a long time, hydrophobic drugs and/or those with relatively high molecular weight for example call for longer retention time since drug release is slow due to the limited solubility in the oral aqueous environment. The low solubility affects both the drug release from the matrix as well as the erosion of the matrix layer, which needs to be adapted to the drug hydrophobicity. Otherwise, the matrix would erode too fast and before the drug is absorbed at the mucosa, releasing the drug into the saliva. Such indirect delivery via the saliva is often unwanted due to the risk of unintended swallowing and loss to the GI system. As outlined above, in order to prevent such drug loss and to ensure a unidirectional release of the active to the mucosa, a backing layer can be used in an oromucosal delivery system to protect the active agent-layer from the saliva.

Multilayer laminates such as those consisting of a backing layer and an active agent-containing layer are commonly prepared by repeated coating and drying of a coating composition consisting of the layer components dissolved or suspended in a solvent. However, this requires the layers to be sufficiently similar in polarity. The backing layer on the other hand needs to be water-insoluble, or at least sparingly water-soluble to be able to protect the underlying active agent layer from being uncovered to the saliva. In case the active agent-containing layer is hydrophilic, direct coating of a backing layer on such hydrophilic active agent layer (or vice versa) is not possible, since the layers would not adhere to each other and detach. In addition, repeated coating and drying also means that the active agent is potentially subjected to repeated thermal stress, which is undesirable in particular for thermolabile actives.

It has been proposed in the past to make use of an adhesive layer comprising a water-soluble polymer such as KollidonR VA64 (a vinylpyrrolidone-vinyl acetate copolymer) to provide the necessary adhesion between two non-adhesive layers, which can be identical or different in polarity but require the presence of a hydrophilic polymer. However, due to the solubility of the polymer, such adhesive layers tend to dissolve after a while so that the backing layer is detached from the active agent layer after all. The inventors have shown that an adhesive layer based on KollidonR VA64 as suggested earlier is not suitable for retention times of over 20 minutes. In addition, in accordance with the past proposal, the non-adhesive layers are required to comprise a hydrophilic polymer, so that backing layers comprising only water-insoluble polymers cannot be used for an adhesive layer based on KollidonR VA64.

In summary, oromucosal therapeutic systems with a long intended retention time and a practically water-insoluble backing layer to protect the active agent layer overcoming the disadvantages outlined above, e.g., providing sufficient adhesion between the layers, are much needed.

OBJECTS AND SUMMARY OF THE INVENTION

It is an object of the present invention to provide an oromucosal therapeutic system overcoming the above-mentioned disadvantages of current systems.

Thus, it is an object of the present invention to provide an oromucosal therapeutic system comprising a backing layer and an active agent layer appropriate for long retention times of up to 60 minutes and more.

It is a further object of the present invention to provide an oromucosal therapeutic system comprising a backing layer and an active agent layer which can be kept adhered to the oral mucosa for a long time such as up to 60 minutes and more without the layers detaching from each other.

It is also a further object of the present invention to provide an oromucosal therapeutic system comprising a backing layer and an active agent layer providing a sufficiently high oromucosal release of the drug.

Another object of the present invention is to provide an oromucosal therapeutic system comprising a backing layer and an active agent layer with identical or different polarity with sufficient inter-layer adhesion.

Another object of the present invention is to provide a means to improve the adhesion between two layers intended for use in an oromucosal therapeutic system, which have the same or different polarity and comprise film-forming polymers which are not hydrophilic.

It is further an object of the present invention to provide an oromucosal therapeutic system which complies with the needs of a convenient application and handling in view of size and thickness, provides for good patient compliance and/or which is easy and cost-efficient to manufacture.

It is also an object of the present invention to provide an oromucosal therapeutic system which can be manufactured without repeated application of heat to dry a coated coating composition.

These objects and others are accomplished by the present invention, which according to one aspect relates to an oromucosal therapeutic system for the oromucosal administration of an active agent comprising a mucoadhesive layer structure comprising A) a backing layer comprising a first film-forming polymer, B) an adhesive layer comprising
a laminating adhesive; and
a first plasticizer, and C) an active agent-containing layer comprising a second film-forming polymer, wherein the laminating adhesive is a mixture comprising polyvinylpyrrolidone and polyvinylacetate, and the first plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

According to another aspect, the invention relates to an adhesive layer, comprising a laminating adhesive; and
a plasticizer,
wherein
the laminating adhesive is a mixture comprising
from 15 to 25 wt-% polyvinylpyrrolidone,
from 70 to 90 wt-% polyvinylacetate, and
about 1 wt-% of one or more stabilizers, and
the plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

According to a further aspect, the invention relates to a bi- or multi-layer laminate, comprising A) a backing layer comprising a first film-forming polymer and B) an adhesive layer comprising
a laminating adhesive; and
a plasticizer, wherein the laminating adhesive is a mixture comprising
from 15 to 25 wt-% polyvinylpyrrolidone,
from 70 to 90 wt-% polyvinylacetate, and
about 1 wt-% of one or more stabilizers, and the plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof, or A) an active agent-containing layer comprising a second film-forming polymer and B) the adhesive layer comprising
a laminating adhesive; and
a plasticizer, wherein the laminating adhesive is a mixture comprising
from 15 to 25 wt-% polyvinylpyrrolidone,
from 70 to 90 wt-% polyvinylacetate, and
about 1 wt-% of one or more stabilizers, and the plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

According to yet another aspect, the invention relates to a process of manufacture of an oromucosal therapeutic system comprising the steps of:

(a) combining at least
a first film-forming polymer and
a solvent
to obtain a backing layer coating composition,
coating the backing layer coating composition onto a release liner and
drying the coated backing layer coating composition to form a backing layer, (b) combining at least
an active agent,
a second film-forming polymer and
a solvent
to obtain an active agent layer coating composition,
coating the active agent layer coating composition onto a release liner and drying the coated active agent layer coating composition to form a single-layer active agent-containing layer, optionally repeating the coating step by coating the active agent layer coating composition on the coated active agent layer coating composition before drying, or on the dried active agent-containing layer to obtain a double-layer active agent-containing layer, (c) combining at least
a laminating adhesive,
a first plasticizer, and
a solvent
to obtain an adhesive layer coating composition, coating the adhesive layer coating composition onto the backing layer obtained in step (a) or the single- or double-layer active agent-containing layer obtained in step (b) and
drying the coated adhesive layer coating composition to form a bi-layer laminate consisting of an adhesive layer and a backing layer on a release liner, or of an adhesive layer and an active agent-containing layer on a release liner, and (d) laminating the bi-layer laminate obtained in step (c) with the single- or double-layer active agent-containing layer obtained in step (b), or with the backing layer obtained
in step (a), respectively, wherein the laminating adhesive is a mixture comprising polyvinylpyrrolidone and polyvinylacetate, and the first plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

According to an even further aspect of the invention, the oromucosal therapeutic system according to the invention is for use in a method of treatment and/or prophylaxis of diseases and medical conditions, preferably in a human patient.

According to another aspect, the invention relates to an oromucosal therapeutic system for the oromucosal administration of an active agent comprising a mucoadhesive layer structure consisting of A) a backing layer comprising
   from 55 to 95 wt-% and preferably about 60 wt-% of ethyl cellulose,
   from 5 to 20 wt-% and preferably about 10 wt-% triacetin,
   from 10 to 35 wt-% and preferably about 30 wt-% of a mixture consisting of
      about 19 wt-% polyvinylpyrrolidone,
      about 80 wt-% polyvinylacetate,
      about 0.8 wt-% sodium lauryl sulfate and
      about 0.2 wt-% of silica, B) an adhesive layer adjacent to the active agent-containing layer on its one side and to the backing layer on its other side, comprising
   from 70 to 90 wt-% and preferably about 80 wt-% of a mixture consisting of,
      about 19 wt-% polyvinylpyrrolidone,
      about 80 wt-% polyvinylacetate,
      about 0.8 wt-% sodium lauryl sulfate and
      about 0.2 wt-% of silica,
   from 10 to 30 wt-%, preferably about 15% of glycerin, and
   from 0 to 10 wt-%, preferably about 5 wt-% of a film-forming polymer selected from the group consisting of ethyl cellulose, hydroxypropyl cellulose, carboxymethyl cellulose sodium, polyvinyl alcohol, hydroxypropyl methyl cellulose, polyvinylpyrrolidone, polyethylene oxide, polyethylene glycol, hydroxyethyl cellulose, methacrylic acid-methyl methacrylate copolymer (1:1) in neutralized form, and any mixture thereof, C) an active agent-containing layer comprising
   an active agent, and
   a second film-forming polymer selected from the group consisting of ethyl cellulose, hydroxypropyl cellulose, carboxymethyl cellulose sodium, polyvinylalcohol, hydroxypropyl methyl cellulose, polyvinylpyrrolidone, polyethylene oxide, polyethylene glycol, hydroxyethyl cellulose, methacrylic acid-methyl methacrylate copolymer (1:1) in neutralized form, and any mixture thereof.

Within the meaning of this invention, the term "oromucosal therapeutic system" or "oromucosal delivery system" refers to a system by which an active agent can be administered, in contrast to a "transmucosal delivery system", not only to the systemic circulation via transmucosal delivery, but also only locally limited (to the mucosa at the administration site and/or to tissue which is adjacent to the administration site) by application to the mucosa of the oral cavity, and refers to the entire individual dosing unit that is applied to the mucosa of a patient, and which comprises a therapeutically effective amount of the active agent in a mucoadhesive layer structure. The mucoadhesive layer structure may be located on a release liner (a detachable protective layer), thus, the oromucosal therapeutic system may further comprise a release liner. In contrast to certain oral thin films which are not necessarily mucoadhesive and which are intended to disintegrate very fast in the saliva (sometimes referred to as "flash wafers"), enteral delivery is unintended and undesirable in oromucosal therapeutic systems.

Within the meaning of this invention, the term "mucoadhesive layer structure" refers to an active agent-containing multi-layer laminate structure providing the area of release for the active agent during administration.

As used herein, the expression "active agent" means a biologically or pharmacologically active compound, which may also be referred to as active, drug substance, drug, active ingredient, active pharmaceutical ingredient (API), or the like. Within the meaning of this invention, the term "therapeutically effective amount" refers to a quantity of active agent in the oromucosal therapeutic system sufficient to provide, if administered by the oromucosal therapeutic system to a patient, the desired therapeutic effect, e.g., as determined by blood levels of a similar range (e.g. of about 10% to about 1000% as measured as an AUC) when compared to blood levels obtained after a one-time administration of approved drug products of the same active agent, or an amount of active similar (e.g. of about 10% to about 1000%) to the amount of active contained in other, topically acting approved drug products of the same active agent.

There are two main types of oromucosal therapeutic systems, i.e. those using backing layers, and those without. As also outlined in the introductory background section, active delivery of an open system type oromucosal therapeutic system using no backing layer will always be a combination of direct delivery from the oromucosal therapeutic system to the mucosa at the adhesion site, and indirect delivery via dissolution of the active from the oromucosal therapeutic system into the saliva, and from the saliva through the mucosa of the oral cavity (and also the stomach or the intestines in case the saliva is swallowed). The proportion of the different delivery routes depends, effects of permeability via the mucosa notwithstanding, mainly on factors such as the solubility of the active and the disintegration time of the oromucosal therapeutic system. The higher the solubility and the faster the disintegration of the oromucosal therapeutic system, the more dissolution into the saliva will be favored over direct delivery into the mucosa at the adhesion site. Such an indirect delivery may have the advantage of providing a practical increase of the mucosal surface area to which the active is released. However, dissolution into the saliva means that the active concentration, and thus the final delivered amount is difficult to control, and the risk of enteral delivery by unintended swallowing of the saliva is serious. The present invention therefore is directed to oromucosal therapeutic systems comprising a backing layer.

Oromucosal therapeutic systems using a backing layer have a completely different approach. In such systems, by using a backing layer, the delivery route is substantially limited to the direct oromucosal delivery, which can be much better controlled, the risk of enteral delivery is reduced, and, even more advantageously, by limiting dissolution of the active agent into the saliva, it is believed that any irritating sensation or bad taste potentially caused by an active agent can be substantially reduced. The challenge for oromucosal therapeutic systems using a backing layer lies in nonetheless providing a sufficient oromucosal delivery of active. Thus, in the sense of the present invention, a "backing layer" is any layer within an oromucosal therapeutic system which is able to prevent (at least a substantial amount of) the active contained within the oromucosal therapeutic system to be dissolved into the saliva. Such a backing layer can be non-dissolvable, or sparingly dissolvable over a prolonged period of time. In the latter case, the time the backing layer takes for dissolution is at least as long as (a substantial amount of) the active takes to be delivered to the mucosa.

The active agent-containing layer may be the final, solidified layer, e.g., obtained after coating and drying the solvent-containing coating composition. The active agent-containing layer may also be manufactured by laminating two or more such solidified layers (e.g., dried layers) of the same composition to provide the desired area weight. The active agent-containing layer may be mucoadhesive (in the form of a mucoadhesive layer) or the oromucosal therapeutic system may comprise an additional mucosa-contacting layer of a mucoadhesive for providing sufficient adhesion. Advantageously, the active agent-containing layer is a mucoadhesive layer.

Within the meaning of this invention, the term "mucoadhesive" refers to a material that in particular adheres to and upon contact with a mucosa, but which preferably is non-tacky and can be touched, e.g., with the fingers and manipulated, e.g., for application into the oral cavity, without unintentionally adhering to the skin of the fingers, when in dry state. A mucoadhesive layer, when in contact with the mucosa, is "self-adhesive", i.e., provides adhesion to the mucosa so that typically no further aid for fixation is needed. The adhesion strength is preferably strong enough that typical movements in the oral cavity are not sufficient to displace a mucoadhesive layer adhered to the mucosa. A "mucoadhesive" layer structure includes a mucoadhesive layer for mucosa contact which may be provided in the form of a mucoadhesive active agent-containing layer or in the form of an additional layer, i.e., a mucoadhesive mucosa-contacting layer.

Within the meaning of this invention, the term "mucosa-contacting layer" refers to a layer included in the oromucosal therapeutic system to be in direct contact with the mucosa of the patient during administration. If the oromucosal therapeutic systems comprises a mucosa-contacting layer as well as one or more other layers, the other layers do not have to contact the mucosa and do not necessarily have mucoadhesive properties. The area of release is provided by the area of the active agent-containing layer. A mucosa-contacting layer which is not at the same time the active agent-containing layer may be used to enhance adherence. The sizes of an additional mucosa-contacting layer and the active agent-containing layer are usually coextensive and correspond to the area of release.

Within the meaning of this invention, the term "area weight" refers to the dry weight of a specific layer, e.g., of the active agent-containing layer, provided in g/m$^2$. The area weight values are subject to a tolerance of ±10%, preferably +7.5% of the nominal value, due to manufacturing variability.

The unit "%" may refer to a percentage given in weight per volume (w/v), volume per volume (v/v) or in weight-%, and, if not indicated otherwise, "%" preferably refers to weight-%.

Within the meaning of this invention, the term "polymer" refers to any substance or material consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2,000, preferably above 5,000 and more preferably above 10,000 Dalton. Correspondingly, compounds with a molecular weight below 2,000, preferably below 5,000 or more preferably below 10,000 Dalton are usually referred to as oligomers.

Within the meaning of this invention, the term "administration" refers to the application of the dosage form, i.e., the oromucosal therapeutic system, to the oral mucosa of the patient, which is then maintained on the mucosa for a specified period of time of administration duration, or until the active agent-containing layer is dissolved, eroded or substantially disintegrated.

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a particular symptom or symptoms suggesting the need for treatment, who is treated preventatively or prophylactically for a condition, or who has been diagnosed with a condition to be treated.

Within the meaning of this invention, the term "coating composition" refers to a composition comprising all components of one of the layers of the mucoadhesive layer structure in a solvent, which may be coated to form the corresponding layer upon drying.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, heptanes, toluene and mixtures thereof.

Within the meaning of this invention, and unless otherwise specified, the term "about" refers to an amount that is ±10% of the disclosed amount. In some embodiments, the term "about" refers to an amount that is ±5% of the disclosed amount. In some embodiments, the term "about" refers to an amount that is ±2% of the disclosed amount.

Within the meaning of this invention, the term "substantial" or "substantially" is used to refer to a large part of the corresponding object or component concerned, e.g., a composition "consisting substantially of" a component comprises a large amount of such a component, such as at least 95% by weight, preferably at least 98% or even at least 99% by weight.

DETAILED DESCRIPTION

Structure of the Oromucosal Therapeutic System

The present invention is related to an oromucosal therapeutic system comprising a mucoadhesive layer structure comprising a backing layer, an adhesive layer and an active agent-containing layer.

The oromucosal therapeutic system is intended to be used for the oromucosal administration of an active agent useful in the treatment and/or prophylaxis of diseases and medical conditions. The backing layer and the active agent-containing layer each comprise a film-forming polymer, and the adhesive layer comprises a laminating adhesive and a plasticizer.

Thus, in accordance with the present invention, the oromucosal therapeutic system for the oromucosal administration of an active agent comprises a mucoadhesive layer structure comprising:

A) a backing layer comprising a first film-forming polymer,

B) an adhesive layer comprising
 a laminating adhesive; and
 a first plasticizer, and C) an active agent-containing layer comprising a second film-forming polymer.

As outlined above, the backing layer prevents the active from being released from the therapeutic system at its non-mucosally adhering surface into the saliva, and thus is considered to be able to prevent or reduce unintended delivery via the gastrointestinal route as well as any irritating sensation or discomfort as well as bad taste an active agent might cause if present in dissolved form in the oral cavity. Further details on the backing layer will be discussed below in a separate chapter.

The adhesive layer serves to keep layers such as the backing layer and the active agent-containing layer adhered to each other. Thus, in certain embodiments, the adhesive layer is adjacent to the active agent-containing layer on its one side and to the backing layer on its other side, i.e., the adhesive layer is "sandwiched" between the backing layer and the active agent-containing layer. The active agent-containing layer, which may be mucoadhesive, may represent the layer that is applied directly to the mucosa.

In certain preferred embodiments, the mucoadhesive layer structure of the oromucosal therapeutic system in accordance with the present invention does not comprise any further layers and consists of the three layers above in view of the ease of manufacture and also in view of keeping the total thickness of the laminate low so as to prevent any patient discomfort. In such a structure, the active agent-containing layer directly contacts the oral mucosa upon administration, i.e., the active agent-containing layer is a mucosa-contacting layer.

In certain other embodiments, the mucoadhesive layer structure may further comprise further layers such as a separate mucosa-contacting layer or cosmetic layers.

Whether provided as an additional layer or not, the mucosa-contacting layer is mucoadhesive and ensures sufficient adhesion to the oral mucosa, preferably for the intended duration of administration and even longer. In contrast to the mucosa-contacting layer, any optional cosmetic layer may provide for a decorative means such as coloring or imprinting, or may simply prevent the patient from touching the backing layer, and is located on top of the mucoadhesive layer structure and is not intended to contact the mucosa.

In view of convenience of manufacture and restricting the overall patch size in terms of surface area, preferably the active agent-containing layer and the adhesive layer, and even more preferably all layers of the mucoadhesive layer structure are coextensive, i.e., identical in shape and size, so that the area of release in such a case corresponds to the area defined by the mucoadhesive layer structure. The mucoadhesive layer structure preferably is large enough to allow a patient convenient manipulating with the fingers without the aid of any specific device such as a tweezer, and a certain minimum size is also required in order to ensure that the laminate does not detach prematurely from the mucosa, and also for being able to include a sufficient amount of active without having to use very thick films. On the other hand, if the laminate is too large, it will be uncomfortable to apply and to wear, leading to low patient compliance. Considering this, in certain embodiments of the invention, the oromucosal therapeutic system has an area of release of at least 0.2 $cm^2$, preferably at least 0.5 $cm^2$, or has an area of release of less than or equal to 10 $cm^2$, preferably less than or equal to 7 $cm^2$, or has an area of release of from 0.2 to 10 $cm^2$, and more preferably of from 0.5 to 7 $cm^2$.

As outlined also above, a mucoadhesive layer structure of an oromucosal therapeutic system consists of one or more thin layers, and thus, in certain embodiments, is in the form of a film. Such a film may have a circular, rectangular or square shape.

The film preferably has a certain degree of thickness, as otherwise it will be difficult to incorporate the required amount of active, and as very thin films are not easy to manufacture, in particular with respect to providing an even thickness. Thus, in certain embodiments, the mucoadhesive layer structure is in the form of a thin film having a total area weight of at least 75 $g/m^2$, preferably at least 100 $g/m^2$, or more preferably at least 130 $g/m^2$. Regarding its thickness, the mucoadhesive layer structure is in the form of a thin film having a total thickness of at least 50 μm, preferably at least 75 μm, and more preferably at least 100 μm. On the other hand, very thick films will be perceived by the patient as disturbing objects in the oral cavity, and thus are disadvantageous in terms of patient compliance. Thus, in certain embodiments, the mucoadhesive layer structure is in the form of a thin film having a total area weight of less than or equal to 700 $g/m^2$, preferably less than or equal to 600 $g/m^2$, or more preferably less than or equal to 500 $g/m^2$. Or, in terms of thickness, the mucoadhesive layer structure is in the form of a thin film having a total thickness of less than 800 μm, preferably less than 700 μm, and more preferably less than 550 μm. In preferred embodiments, the mucoadhesive layer structure is in the form of a thin film having a total area weight of from 75 to 700 $g/m^2$, preferably from 100 to 600 $g/m^2$, or more preferably from 130 to 500 $g/m^2$, or having a total thickness from 50 to 800 μm, preferably from 75 to 700 μm, and more preferably from 100 to 550 μm.

The oromucosal therapeutic system according to the invention is normally stored in a seam-sealed pouch without any further means of protection. However, the mucoadhesive layer structure may also be located on a detachable protective layer (release liner) from which it is removed immediately before application to the mucosa of the patient's oral cavity. Thus, the oromucosal therapeutic system may or may not further comprise a release liner. An oromucosal therapeutic system protected by a release liner is usually also stored in a seam-sealed pouch. The packaging may be child resistant and/or senior friendly.

Adhesive Layer and Laminating Adhesive

As outlined in more detail above, the oromucosal therapeutic system according to the present invention comprises a mucoadhesive layer structure comprising an adhesive layer. As outlined above, adhesive layers proposed in the past for use in multilayer laminates for mucosal application dissolved too fast in saliva so that they were not suitable for longer administration, and also were not suitable for use in systems comprising hydrophobic layers such as water-insoluble backing layers.

The adhesive layer used in the present invention solves this issue by combining low solubility in aqueous media and excellent adhesive properties in particular with respect to adjacent (non-adhesive) layers, which may also be of hydrophobic nature and, e.g., need not comprise a hydrophilic polymer.

Low solubility as used herein means that the adhesive layer withstands dissolution in aqueous media such as saliva for a sufficient duration, e.g., in preferred embodiments, an adhesive layer according to the present invention, if provided in a mucoadhesive layer structure between two other (non-adhesive) layers such as backing layer, active agent-containing layer or other mucosa-contacting layers, will retain integrity if placed in natural or artificial saliva for at least 30 minutes, preferably for at least 60 minutes.

Excellent adhesive properties means that a multilayer-laminate obtained from laminating the adhesive layer between two other (non-adhesive) layers such as backing layer, active agent-containing layer or other mucosa-contacting layers, will not show any layer separation. In preferred embodiments, layer separation in such a laminate will require deliberate attempts of manual separation and the laminate will withstand manual separation of the layers unless a corner of the system is bent to create a folded "peel tab". In certain further preferred embodiments, the adhesive layer provides excellent adhesive properties upon lamination with further layers but is still non-tacky to touch, which is of advantage for handling, as, e.g., during manufacture of the mucoadhesive layer structure, the operator does not need to be concerned about unintentional adhering of the adhesive layer to the fingers, hands, or to other surfaces when manipulating the adhesive layer.

In terms of size (i.e., the surface area), the adhesive layer may in particular be of the same size as the remaining layers of the mucoadhesive layer structure such as the backing layer and the active agent-containing layer, and preferably is of the same size as at least one of the layers adjacent to the adhesive layer. Thus, in certain embodiments, the adhesive layer and the backing layer and/or the active agent-containing layer are coextensive in shape and size.

With respect to the area weight of the adhesive layer, a certain thickness is required in order to provide for sufficient adhesive properties. On the other hand, the adhesive layer is preferably thin enough so that the total thickness of the oromucosal therapeutic system is such that it is not uncomfortable upon administration in the oral cavity. Thus, in certain embodiments, the adhesive layer has an area weight of at least 30 g/m$^2$, preferably at least 50 g/m$^2$ and more preferably of about 60 g/m$^2$, or of less than 100 g/m$^2$ and preferably less than 80 g/m$^2$. As also indicated above, the adhesive layer comprises a laminating adhesive. The laminating adhesive is the main component of the adhesive layer and provides for the adhesive properties. As such, the laminating adhesive is comprised in the adhesive layer in an amount appropriate to provide sufficient adhesiveness, and in certain embodiments, the adhesive layer comprises from 50 to 90 wt-% and preferably from 60 to 85 wt-% of the laminating adhesive.

In accordance with the present invention, the laminating adhesive is a mixture comprising polyvinylpyrrolidone and polyvinylacetate, and preferably, the mixture consists substantially of polyvinylpyrrolidone and polyvinylacetate. The hydrophobic polyvinylacetate is the predominating component and without wishing to be bound by theory, it is assumed that this allows a sufficient adhesion to be achieved also when the adhesive layer is used to laminate relatively hydrophobic layers comprising no hydrophilic polymers. Thus, in certain preferred embodiments, the mixture comprises from 70 to 90 wt-%, preferably from 75 to 85 wt-% and more preferably about 80 wt-% polyvinylacetate. The amount of polyvinylpyrrolidone is correspondingly lower, thus, in certain preferred embodiments, the mixture comprises from 10 to 30 wt-%, preferably from 15 to 25 wt-% and more preferably about 19 wt-% polyvinylpyrrolidone.

In certain embodiments, the polyvinylpyrrolidone is selected from soluble polyvinylpyrrolidones and preferably is selected from polyvinylpyrrolidones having a K-Value of from 28 to 32, and/or a molecular weight of from 44,000 to 54,000 and preferably of about 50,000 as measured by SEC using a detection system not requiring reference standards. Such polyvinylpyrrolidones are commercially available under the brand name KollidonR 30 from BASF.

In certain embodiments, the polyvinylacetate has an average molecular weight Mw of from 400,000 to 500,000 and preferably of about 450,000.

In certain embodiments, the mixture may comprise further conventional excipients, and in particular may comprise one or more stabilizers. In certain preferred embodiments, the mixture comprises about 1 wt-% of one or more stabilizers, and preferably comprises about 0.8 wt-% sodium lauryl sulfate and about 0.2 wt-% of silica as stabilizers.

Thus, in an even more preferred embodiment, the mixture comprises from 10 to 30 wt-%, preferably from 15 to 25 wt-% and more preferably about 19 wt-% polyvinylpyrrolidone, from 70 to 90 wt-%, preferably from 75 to 85 wt-% and more preferably about 80 wt-% polyvinylacetate, and about 1 wt-% of one or more stabilizers, and preferably about 0.8 wt-% sodium lauryl sulfate and about 0.2 wt-% of silica as stabilizers.

The average molecular weight of the mixture may be expressed as K-value according to a method described in the monographs "Povidone" and measured in a 1% solution in tetrahydrofuran. In an also preferred embodiment, the mixture has such a K-value of from 60 to 68 and/or a glass transition temperature Tg of about 35° C.

Such mixtures are commercially available under the brand name KollidonR SR from BASF which has the further advantage of the mixture being readily at hand and not necessitating a further, time-consuming step of preparing the mixture by combining the individual components.

As also indicated above, the adhesive layer also comprises a plasticizer. The plasticizer serves to increase flexibility and plasticity of the laminating adhesive and is required for achieving appropriate adhesive properties. The plasticizer is therefore also comprised in the adhesive layer in an amount appropriate to provide, together with the laminating adhesive, sufficient adhesiveness. This plasticizer is also referred to as "first" plasticizer herein to distinguish between the plasticizers used in the different layers of the mucoadhesive layer structure, e.g., the plasticizer contained in the backing layer is referred to as "second" plasticizer. In certain embodiments, the adhesive layer comprises from 10 to 45 wt-% and preferably about 15 wt-% of the first plasticizer.

In accordance with the present invention, the first plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

As will be also apparent from the examples, the inventors have found out that the adhesive properties can be further enhanced by including a film-forming polymer, however, high amounts of (e.g., hydrophobic) film-forming polymers may result in brittleness of the film, so that the amount is preferably limited. Thus, in certain embodiments, the adhesive layer comprises a film-forming polymer, preferably in an amount of 0 to 10 wt-%, and even more preferably in an amount of about 5 wt-% of the adhesive layer. The film-forming polymer is not particularly limited and can in particular be selected from any of the film-forming polymers listed further below in a separate chapter. In preferred embodiments, the film-forming polymer comprised in the adhesive layer is selected from ethyl celluloses and/or hydroxypropyl celluloses, in particular those as defined further below. It is further preferred that the film-forming polymer in the adhesive layer is identical to those contained in the layers adjacent to the adhesive layer, i.e. the first film-forming polymer of the backing layer and/or the second film-forming polymer of the active agent-containing layer.

Thus, in certain particularly preferred embodiments, the adhesive layer comprises

- from 50 to 90 wt-%, preferably from 60 to 85 wt-% of the laminating adhesive,
- from 10 to 45 wt-%, preferably about 15 wt-% of the first plasticizer, and
- from 0 to 10 wt-%, preferably about 5 wt-% of the first and/or second film-forming polymer each.

As will be appreciated further below in more detail, in certain embodiments, it is preferable that the adhesive layer coating composition for preparing the adhesive layer makes use of certain organic solvents, i.e., the adhesive layer according to the present invention may be obtainable by combining the laminating adhesive, the first plasticizer and optionally a film-forming polymer and further optional excipients in a solvent selected from ethanol, ethyl acetate, acetone and any mixture thereof, preferably in a solvent selected from ethanol, ethyl acetate, acetone and a mixture of acetone and ethanol, casting the obtained composition on the backing layer or one of the other layers of the mucoadhesive layer structure, and drying the casted film.

In certain aspects, the present invention is also directed to the adhesive layer as such. As outlined above, the inventive adhesive layer is advantageous in that it provides excellent adhesive properties upon lamination with further layers but is still non-tacky to touch, and does not require any addition of a solvent or other adhesive aids and can be used for dry bond laminating. Thus, in accordance with such aspect, the present invention is also related to an adhesive layer, comprising a laminating adhesive; and
a plasticizer wherein the laminating adhesive is a mixture comprising
from 15 to 25 wt-% polyvinylpyrrolidone,
from 70 to 90 wt-% polyvinylacetate, and
about 1 wt-% of one or more stabilizers, and the plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

In certain further aspects, the present invention is also directed to the use of such an adhesive layer in a method of laminating as well as to a method of laminating of two (non-adhesive) layers with the aid of such an adhesive layer, as will be described in more detail further below.

In such an inventive adhesive layer and uses thereof, further preferred characteristics concerning the adhesive layer and its components such as the laminating adhesive and the plasticizer are identical to those described further above for the adhesive layer as part of the inventive oromucosal therapeutic system.

In certain yet further aspects, the present invention is also directed to a bi- or multi-layer laminate comprising such an adhesive layer. The inventive bi-layer laminate can be prepared by coating and drying an adhesive layer composition on the backing layer of an oromucosal therapeutic system, and used for laminating with different further layers. The inventive adhesive layer can also be used for laminating two active agent-containing layers, where necessary (e.g., in order to provide for a sufficient amount of active), wherein the active agent-containing layers may be identical or different, e.g., in terms of composition, the active agent, the active agent amount or concentration, and/or the active release profile. Thus, in further aspects, the present invention is also directed to bi- or multi-layer laminates comprising an adhesive layer as described above and one or two active agent-containing layers which are adjacent to the adhesive layer, wherein the bi-layer laminate with one active agent-containing layer can be used for laminating with another active agent-containing layer to obtain a multi-layer laminate with two active agent-containing layers.

In accordance with such aspects, the present invention is directed to a bi- or multi-layer laminate, comprising A) a backing layer comprising a first film-forming polymer and
B) an adhesive layer comprising
a laminating adhesive; and
a plasticizer, wherein the laminating adhesive is a mixture comprising
from 15 to 25 wt-% polyvinylpyrrolidone,
from 70 to 90 wt-% polyvinylacetate, and
about 1 wt-% of one or more stabilizers, and the plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof, or A) an active agent-containing layer comprising a second film-forming polymer and
B) the adhesive layer comprising
a laminating adhesive; and
a plasticizer, wherein the laminating adhesive is a mixture comprising
from 15 to 25 wt-% polyvinylpyrrolidone,
from 70 to 90 wt-% polyvinylacetate, and
about 1 wt-% of one or more stabilizers, and the plasticizer is selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof.

In certain additional aspects, the present invention is also directed to the use of such a bi- or multi-layer laminate in a method of laminating as well as to a method of laminating of such a bi- or multi-layer laminate with a further (non-adhesive) layer, as will be described in more detail further below.

In all the above aspects concerning bi- or multi-layer laminates comprising the inventive adhesive layer, and uses as well as methods making use thereof, further preferred characteristics concerning bi- or multi-layer laminate, the adhesive layer and its components such as the laminating adhesive and the plasticizer are identical to those described further above for the bi- or multi-layer laminate and in particular the adhesive layer as part of the inventive oromucosal therapeutic system.

Backing Layer

As outlined above in more detail, the oromucosal therapeutic system according to the present invention comprises a mucoadhesive layer structure comprising a backing layer. The backing layer comprises a film-forming polymer.

Since the backing layer is used to prevent (at least a substantial amount of) the active to be dissolved into the saliva, the backing layer preferably is water-insoluble, or may be sparingly water-soluble and the time the backing layer takes for dissolution is at least as long the active takes to be delivered through the mucosa, e.g., as long as the active agent-containing layer takes for dissolving. Water-insoluble here means that the backing layer does not dissolve in any aqueous environment, in particular in human saliva. In certain embodiments, the backing layer also does not swell by absorbing water. It is of course preferred that the backing layer is active agent-free, i.e., in preferred embodiments, the backing layer does not comprise any substantial amounts of any active agent, and in particular comprises less than 1% and preferably less than 0.1% of any active agent, preferably the one contained in the active agent layer.

In terms of surface area size, the backing layer may in particular be of the same size as or larger than the active agent-containing layer. Thus, in certain embodiments, the backing layer and the active agent-containing layer are coextensive in shape and size, while in other embodiments, the backing layer is larger in size than and extends the surface area of the active agent-containing layer. While a mucoadhesive layer structure with the same size of backing and active agent-containing layer are more easy to manufacture since a multi-layer laminate can be diecut to provide the mucoadhesive layer structure, a mucoadhesive layer structure with a backing layer that is larger than the active agent-containing layer is more difficult to manufacture, but also provides the advantage that there is less risk of the active leaking, since the edge of the active agent-containing layer will also be covered by the backing layer.

With respect to the area weight of the backing layer, a certain thickness is required in order to provide for sufficient protection of active, and in addition, it is also difficult to coat very thin layers in particular with sufficient accuracy. On the other hand, thick layers may not only provoke an uncomfortable feeling in the oral cavity but are also difficult to manufacture. On balance, it is preferred that the backing layer has an area weight of at least 20 $g/m^2$, preferably at least 40 $g/m^2$ and more preferably of about 50 $g/m^2$, or of less than 100 $g/m^2$, preferably less than 70 $g/m^2$.

The backing layer comprises a film-forming polymer that serves as a matrix for providing sufficient cohesive properties of the layer. This film-forming polymer is also referred to as "first" film-forming polymer herein to distinguish between the film-forming polymers used in the different layers of the mucoadhesive layer structure, e.g., the film-forming polymer contained in the active-agent containing layer is referred to as "second" film-forming polymer. Polymers that can be used as film-forming polymer, and in particular as "first" film-forming polymer are described further below. The amount of film-forming polymer in the backing layer should be appropriate to provide a layer of sufficient mechanical stability and low water-solubility. Thus, in certain embodiments, the backing layer comprises from 55 to 95 wt-% and preferably about 60 wt-% of the first film-forming polymer. In other embodiments, where the backing layer does not comprise substantial amounts of further excipients, in particular polymers such as the laminating adhesive aid discussed further below, the backing layer may comprise from 70 to 90 wt-%, and preferably about 80 wt-% of the first film-forming polymer.

The backing layer may comprise, in addition to the (first) film-forming polymer a plasticizer (which is then referred to as "second" plasticizer) and/or a laminating adhesive aid. As will be apparent from the examples, appropriate use of such second plasticizer and/or a laminating adhesive aid will result in an improved adhesion of the laminate.

Thus, in certain embodiments, the backing layer comprises a plasticizer, preferably in an amount of 5 to 20 wt-%, and even more preferably in an amount of about 10 wt-% of the backing layer. Such a plasticizer, if present in the backing layer, is preferably selected from the group consisting of mono-, di-, oligo- and polysaccharides and derivatives thereof such as polyethylene glycol, triacetin, triethyl citrate, tributyl citrate, propylene glycol, glycerin, medium chain triglycerides and any mixture thereof. In terms of improved adhesion, the plasticizer, if present in the backing layer, is more preferably glycerin, triacetin or any mixture thereof, and most preferably is triacetin.

As indicated above, in certain embodiments, the backing layer comprises a laminating adhesive aid, preferably in an amount of up to 60 wt-%, or more preferably from 10 to 35 wt-% of the backing layer. Such a laminating adhesive aid, if present in the backing layer, is preferably a mixture consisting substantially of polyvinylpyrrolidone and polyvinylacetate, which more preferably is identical to the laminating adhesive contained in the adhesive layer. As will be shown in the examples, such preferred laminating adhesive aids will further enhance the adhesive properties of the laminate.

Considering the stability of the backing layer with respect to its composition, it is preferable that the backing layer does not comprise any volatile constituents, which bear the risk of evaporating and changing the composition upon storage or of being digested and potentially resulting in health concerns of the patient. Thus, in certain embodiments, the backing layer comprises substantially no (volatile) solvent such as methanol, ethanol, acetone, 1-propanol, 2-propanol, ethyl acetate, hexane, n-heptane, and any mixtures thereof, and in particular, the backing layer comprises less than or equal to 5 wt-%, preferably less than or equal to 3 wt-%, and more preferably less than or equal to 1 wt-% of such a solvent.

Active Agent-Containing Layer

As outlined in more detail above, the oromucosal therapeutic system according to the present invention comprises a mucoadhesive layer structure comprising an active agent-containing layer. The active agent-containing layer comprises the active agent and a film-forming polymer.

As outlined above, the active agent-containing layer preferably is a mucosa-contacting layer and in such specific embodiments needs to provide for sufficient mucoadhesion during the period of administration. Thus, depending on the active agent and the time it takes to be delivered, the mucoadhesive properties need to be maintained for a sufficiently long period of time. These can, e.g., reach 30 minutes, 60 minutes or even longer, in particular for hydrophobic active agents. The film-forming polymer of the active agent-containing layer needs to be correspondingly chosen to ensure proper mucoadhesive properties, but also in view of potential dissolution or disintegration in the saliva. In certain embodiments, the active agent-containing layer disintegrates over time to release the active, but maintains integrity for the duration of administration, e.g., for at least 30 minutes, 60 minutes or even longer.

As described above in the sections concerning the adhesive layer and the backing layer, these layers may be of the same shape and size as the active agent-containing layer, while in other embodiments, the backing layer is larger in size than and extends the surface area of the active agent-containing layer. In the simplest way and also in accordance with a preferred embodiment, all three layers are coextensive in shape and size.

With respect to the area weight of the active agent-containing layer, a certain minimum thickness is normally required to include a therapeutically effective amount of the active agent without the oromucosal therapeutic system becoming too large, in particular in case the solubility of the active agent is low. Taking into account that the total thickness of the system should be such that it does not cause any discomfort to the patient, it is preferred that the active agent-containing layer has an area weight of at least 50 g/m$^2$, preferably at least 100 g/m$^2$ and more preferably of about 150 g/m$^2$, or of less than 500 g/m$^2$, or of less than 200 g/m$^2$. Such relatively thick layers can be prepared by repeating the coating and drying of the active agent layer coating composition, e.g., as will be shown in the examples, a 150 g/m$^2$ layer can be prepared by coating and drying the coating composition two times in such amount that an area weight of 75 g/m$^2$ is achieved each time. In other words, such double (or multi-) layers prepared by repeating the coating and drying of an active agent layer coating composition will be regarded as the active agent-containing layer in the sense of the present invention. Alternatively, a further adhesive layer could be used to laminate two layers.

As outlined above, the active agent-containing layer comprises a film-forming polymer which is referred to as "second" film-forming polymer and which serves as a matrix for providing sufficient cohesive properties of the layer. Polymers that can be used as film-forming polymer, and in particular as "second" film-forming polymer are described further below. The amount of film-forming polymer in the active agent-containing layer should be appropriate to provide a layer with proper mucoadhesive properties, but also in view of potential dissolution or disintegration in the saliva. Thus, in certain embodiments, the second film-forming polymer is comprised in the active agent-containing layer in a total amount of 70 to 90 wt-% and even more preferably of about 80 wt-% of the active agent-containing layer, and, in particular in case of a mixture of polymers, is comprised in an amount per polymer of 5 to 50 wt-% and preferably 10 to 40 wt-% of the active agent-containing layer.

In addition to the second film-forming polymer and the active agent, the active agent-containing layer may comprise further excipients known to the person skilled in the art and as also listed further below, such as a plasticizer or a colorant.

Active Agent

In accordance with the invention, the oromucosal therapeutic system comprises a therapeutically effective amount of the active agent in a mucoadhesive layer structure. In preferred embodiments, substantially all of the active agent is comprised in the active agent-containing layer described above.

The active agent is not particularly limited as long as it is suitable for oromucosal delivery. Since the inventive adhesive layer allows using a backing layer protecting the active agent-containing layer from being dissolved, active agents with a bad taste or those causing irritating sensations in the oral cavity can also be used. Since the oromucosal therapeutic system can be designed and adapted to a long period of administration, it is particularly suitable for active agents that require a long time to be delivered, e.g., active agents which are substantially insoluble or sparingly soluble in aqueous media such as water or saliva, or which have a relatively high molecular weight. Such active agents are known to the person skilled in the art and can be selected appropriately.

Film-Forming Polymers

As outlined in more detail above, the oromucosal therapeutic system according to the present invention comprises a mucoadhesive layer structure comprising a backing layer, an adhesive layer and an active agent-containing layer, and the backing layer and the active agent-containing layer both comprise a film-forming polymer.

The film-forming polymers that can be used in the present invention are not particularly limited and any known polymer with film-forming properties, preferably those that are pharmaceutically acceptable (and, e.g., are approved for pharmaceutical applications), can be employed.

Exemplary film-forming polymers that can be used in the present invention are, e.g., ethyl cellulose (commercially available under the brand name Aqualon™ ethylcellulose from Ashland), copolymers based on dimethylaminoethyl methacrylate, butyl methacrylate and methyl methacrylate (commercially available under the brand name EudragitR E100 from Evonik), hydroxypropyl cellulose (commercially available under the brand name Klucel™ from Ashland), carboxymethyl cellulose sodium (commercially available under the brand name Blanose™ from Ashland), polyvinyl alcohol (commercially available under the brand name Poval™ from Kuraray), hydroxypropyl methyl cellulose, polyvinylpyrrolidone, polyethylene oxide, polyethylene glycol, hydroxyethyl cellulose, methacrylic acid-methyl methacrylate copolymer (1:1) (commercially available under the brand name EudragitR L100 from Evonik) in neutralized form, and any mixture thereof.

In certain preferred embodiments, the ethyl cellulose has

- a viscosity as measured as a 5% solution at 25° C. in 80:20 toluene:ethanol by weight in accordance with ASTM D914 of from 30 to 60 mPa·s, more preferably from 40 to 52 mPa·s, and/or
- a substitution of ethoxyl groups of 48.0 to 49.5% as measured in accordance with ASTM D914, and/or
- a moisture content of 3% by weight or less in accordance with ASTM D914.

Such ethyl cellulose is commercially available from Ashland Specialty Ingredients and corresponds to the grade ethyl cellulose N50NF.

Hydroxypropyl cellulose is commercially available from Ashland under the brand name Klucel™ and is provided in several grades.

The grades differ from each other by molecular weight Mw (as measured by GPC-size exclusion chromatography) and Brookfield viscosity (25° C., LVF, Moisture Free), and are as follows:

- The HF grade has a Mw of 1,150,000 and a Brookfield Viscosity of 1,500-3,000 mPa·s (1% in water),
- the MF grade has a Mw of 850,000 and a Brookfield Viscosity of 4,000-6,500 mPa·s (2% in water),
- the GF grade has a Mw of 370,000 and a Brookfield Viscosity of 150-400 mPa·s (2% in water),
- the JF grade has a Mw of 140,000 and a Brookfield Viscosity of 150-400 mPa·s (5% in water),
- the LF grade has a Mw of 95,000 and a Brookfield Viscosity of 75-150 mPa·s (5% in water), the EF grade has a Mw of 80,000 and a Brookfield Viscosity of 300-600 mPa·s (10% in water), the ELF grade has a Mw of 40,000 and a Brookfield Viscosity of 150-300 mPa·s (10% in water).

Thus, in certain embodiments, the hydroxypropyl cellulose has a molecular weight (as measured by GPC-size exclusion chromatography) of from 30,000 to 1,500,000, and in particular, the hydroxypropyl cellulose has a molecular weight (as measured by GPC-size exclusion chromatography) selected from between 35,000 and 45,000, in particular 40,000
between 75,000 and 85,000, in particular 80,000
between 90,000 and 100,000, in particular 95,000
between 130,000 and 150,000, in particular 140,000
between 350,000 and 400,000, in particular 370,000,
between 800,000 and 900,000, in particular 850,000, and
between 1,100,000 and 1,200,000, in particular 1,150,000.

In preferred embodiments, the hydroxypropyl cellulose has:

a Mw of about 370,000 and a Brookfield Viscosity of 150-400 mPa·s (2% in water), or a Mw of about 80,000 and a Brookfield Viscosity of 300-600 mPa·s (10% in water).

Sodium carboxymethyl cellulose (CMC) is commercially available from Ashland under the brand name Blanose™ and is provided in several grades.

The grades differ from each other, e.g., by degree of substitution, by weight average molecular weight and viscosity (mPa·s). Herein preferred is a grade that is referred to as 7LP EP and has a degree of substitution of 0.7, a weight average molecular weight of 90,500 and a viscosity of 25-50 mPa·s.

Polyvinyl alcohol (PVA) is commercially available from Merck KGaA under the brand name Mowiol™ and is provided in several grades.

The grades differ from each other, e.g., by degree of hydrolysis and viscosity (mPa·s). Herein preferred is a grade that is referred to as 40-88 and has a degree of hydrolysis of 87.0 to 89.0 mol % and a viscosity of 38.0 to 42.0 mPa·s.

In certain embodiments, the first film-forming polymer, i.e., the film-forming polymer comprised in the backing layer is selected from the group consisting of ethyl cellulose, a copolymer based on dimethylaminoethyl methacrylate, butyl methacrylate and methyl methacrylate, and any mixtures thereof, and preferably is ethyl cellulose of N50NF grade as described above.

In certain embodiments, the second film-forming polymer, i.e., the film-forming polymer comprised in the active agent-containing layer, is selected from the group consisting of ethyl cellulose, hydroxypropyl cellulose, carboxymethyl cellulose sodium, polyvinyl alcohol, hydroxypropyl methyl cellulose, polyvinylpyrrolidone, polyethylene oxide, polyethylene glycol, hydroxyethyl cellulose, methacrylic acid-methyl methacrylate copolymer (1:1) in neutralized form, and any mixture thereof, and more preferably is a mixture of polyvinyl alcohol, carboxymethyl cellulose sodium and hydroxypropyl cellulose. In the second film-forming polymer, the hydroxypropyl cellulose is preferably of grade GF as described above.

In certain embodiments, the adhesive layer also comprises a film-forming polymer, which preferably is identical to the first and/or the second film-forming polymer. In other words, in certain embodiments, the adhesive layer comprises a film-forming polymer selected from the group consisting of ethyl cellulose and hydroxypropyl cellulose. Where used as a film-forming polymer in the adhesive layer, the hydroxypropyl cellulose is preferably of grade EF as described above and the ethyl cellulose is of N50NF grade as described above.

Plasticizer

As outlined in more detail above, the oromucosal therapeutic system according to the present invention comprises a mucoadhesive layer structure comprising a backing layer, an adhesive layer and an active agent-containing layer, wherein the adhesive layer comprises a plasticizer, and the backing layer and the active agent-containing layer may also comprise a plasticizer.

The plasticizers that can be used in the present invention are not particularly limited and any plasticizer known to the person skilled in the art, preferably those that are pharmaceutically acceptable (and, e.g., are approved for pharmaceutical applications), can be employed.

Exemplary plasticizers that can be used in the present invention are, e.g., mono-, di-, oligo- and polysaccharides and derivatives thereof such as polyethylene glycol, triacetin, triethyl citrate, tributyl citrate, propylene glycol, glycerin, medium chain triglycerides and any mixture thereof.

Where used in the adhesive layer, the plasticizer is referred to as first plasticizer, and is preferably glycerin, triacetin or any mixture thereof, and more preferably is glycerin. The first plasticizer is preferably used in an amount of from 10 to 45 wt-%, and more preferably of about 15 wt-% of the adhesive layer.

Where used in the backing layer, the plasticizer is referred to as second plasticizer, and is preferably glycerin, triacetin or any mixture thereof, and more preferably is triacetin. The second plasticizer is preferably used in an amount of 5 to 20 wt-%, and even more preferably in an amount of about 10 wt-% of the backing layer.

Where used in the active agent-containing layer, the plasticizer is preferably glycerin, triacetin or any mixture thereof, and more preferably is glycerin preferably used in an amount of 1 to 10 wt-%, and even more preferably in an amount of 2 to 5 wt-% of the active agent-containing layer.

Further Excipients

The layers of the oromucosal therapeutic system according to the invention may each comprise further excipients selected from the group consisting of fatty acids, taste-masking agents, sweeteners, flavoring agents, colorants, permeation enhancers, solubilizers, humectants, disintegrants, emulsifiers, antioxidants, stabilizers, buffer reagents and further film-forming polymers.

Such excipients may be present in the layer concerned in an amount of from 0.001 to 15 wt-% of the layer per additive. In a certain embodiment, the total amount of all additives is from 0.001 to 25 wt-% of the layer.

In certain embodiments, the colorant may be selected from the group consisting of titanium dioxide, brilliant blue FCF, indigo carmine, fast green FCF, erythrosine, allura red AC, tartrazine and sunset yellow FCF, curcumin, riboflavin, rivoflavin-5'-phosphate, quinoline yellow, orange yellow S, cochineal, carminic acid, azorubine, carmoisine, amaranth, ponceau 4R, cochineal red A, patent blue V, indigotine, chlorophylls, chlorophyllins, copper complexes of chlorophyll and chlorophyllins, green S, plain caramel, caustic sulphite caramel, ammonia caramel, sulphite ammonia caramel, brilliant black BN, black PN, vegetable carbon, brown HT, carotenes, annatto, bixin, norbixin, paprika extract, capsanthian, capsorubin, lycopene, beta-apo-8'-carotenal, lutein, canthaxanthin, beetroot red, betanin, anthocyanins, calcium carbonate, iron oxides and hydroxides, aluminium, silver, gold and litholrubine BK.

In certain embodiments, the antioxidant may be selected from BHT and vitamin E (α-tocopherol).

In certain embodiments, the stabilizer may be selected from chelating agents such as organic acids selected from mono-, di-, oligo and polycarboxylic acids, for example succinic acid, citric acid, tartaric acid, acrylic acid, benzoic acid, malic acid, maleic acid, oxalic acid, sorbic acid and mixtures thereof.

Method of Treatment/Medical Use

In accordance with a specific aspect of the present invention, the oromucosal therapeutic system according to the invention is for use in a method of treatment and/or prophylaxis of diseases and medical conditions, preferably in a human patient.

According to a specific aspect, the present invention is also directed to a method of treatment and/or prophylaxis of diseases and medical conditions, wherein the oromucosal therapeutic system according to the invention is administered to a patient, and preferably a human patient.

According to a specific aspect, the present invention is also directed to the use of the inventive oromucosal therapeutic system for the manufacture of a medicament for the treatment and/or prophylaxis of diseases and medical conditions, preferably in a human patient.

The oromucosal therapeutic system is preferably administered by applying the mucoadhesive layer structure to the mucosa of the oral cavity of a human patient and maintained on the mucosa for a certain period of time (the administration period). In case of insoluble backing layers or those that have such a low solubility that it is not completely dissolved during the administration period, the backing layer needs to be removed from the administration site after the administration period or swallowed. Likewise, as KollidonR SR will swell in saliva, but not (at least not completely) dissolve, the adhesive layer will also have to be removed or swallowed. In preferred embodiments, the oromucosal therapeutic system is administered by applying the mucoadhesive layer structure to the buccal, sublingual, gingival or palatal mucosa of the oral cavity of a human patient. The administration period may be as short as less than a minute, or several minutes, such as from 1 to 10 minutes, a little longer, such as 10 to 30 minutes, or even extended such as from 30 minutes to 60 minutes and even longer.

Process of Manufacture

The invention further relates to a process of manufacture of an oromucosal therapeutic system, and in particular of the inventive oromucosal therapeutic system as outlined above. In accordance with one aspect, the invention also relates to a process of manufacture of a bi- or multi-layer laminate comprising an adhesive layer as described above.

In such a process of manufacture, a coating composition is prepared for each of a backing layer, an active agent-containing layer and an adhesive layer, by combining all of the layer components with a solvent. The backing layer and active agent-containing layer are then prepared by coating and drying the backing layer coating composition as well as the active agent layer coating composition on a release liner (which can be an intermediate release liner that is later removed), and a bi-layer laminate is obtained by coating and drying the adhesive layer on the backing layer. The thus prepared bi-layer laminate can then be laminated with the active agent-containing layer using, e.g., a conventional lamination station. Lamination preferably does not require the use of a solvent and is thus referred to as "dry bond laminating". In yet another preferred embodiment, lamination can also be conducted without application of heat, and thus is advantageous in that the active agent is not subjected to thermal stress.

To summarize, the inventive process of manufacture of an oromucosal therapeutic system comprises the steps of (a) combining at least the backing layer components as described above and a solvent to obtain a backing layer coating composition, coating the backing layer coating composition onto a release liner and drying the coated backing layer coating composition to form a backing layer, (b) combining at least the active agent layer components as described above and a solvent to obtain an active agent layer coating composition coating the active agent layer coating composition onto a release liner and drying the coated active agent layer coating composition to form an active agent-containing layer, (c) combining at least the adhesive layer components as described above and a solvent to obtain an adhesive layer coating composition coating the adhesive layer coating composition onto the backing layer obtained in step (a) and drying the coated adhesive layer coating composition to form a bi-layer laminate consisting of an adhesive layer and a backing layer on a release liner, and (d) laminating the bi-layer laminate obtained in step (c) with the active agent-containing layer obtained in step (b).

In step (b), the coating step is optionally repeated by coating the active agent layer coating composition on the coated active agent layer coating composition before drying, or on the dried active agent-containing layer to obtain a double-layer active agent-containing layer.

In steps (a) and (b), the release liner in preferred embodiments is an intermediate release liner that can later be removed. In all steps, the drying time is adapted in view of the solvent and matrix polymer used. In step (c), preferably the drying step is conducted only as long as it is necessary to obtain a surface which is dry to touch. Without wishing to be bound by theory, the adhesive layer in such a case may still contain some residual amount of solvent which may be beneficial for the consecutive dry bond laminating step in that a good adhesion can be achieved.

The inventive bi- or multi-layer laminate for use in laminating can be prepared by an analogous process which, however, comprises only steps (a) to (c) and omits (obviously) the laminating step (d).

In such inventive processes, the features of the components used as well as the layers obtained are preferably as outlined above in the corresponding chapters.

The solvent used in each of the steps are not particularly limited, but in view of ease of coating, it is preferred that the solvent is able to dissolve substantially all of the layer components except optional inorganic components such as titanium dioxide in case an organic solvent is used. In preferred embodiments, the solvent used in step (a) for the backing layer is selected from organic solvents and preferably is ethanol or a solution of ethanol and acetone. In preferred embodiments, the solvent used in step (b) for the active agent-containing layer is selected from aqueous solvents such as water and ethanol, and more preferably is water. In yet preferred embodiments, the solvent used in step (c) for the adhesive layer is selected from organic solvents, preferably from the group consisting of ethanol, ethyl acetate, acetone and any mixtures thereof, and preferably is ethyl acetate, acetone, or a solution of acetone and ethanol, preferably at a ratio of 6:4 to 9:1. Ethanol as solvent might lead to some tack of the obtained adhesive layer, in particular where the amount of plasticizer is high, and thus it is preferred not to use pure ethanol for step (c).

Finally, in accordance with one aspect, the present invention is also directed to an oromucosal therapeutic system or a bi- or multi-layer laminate that is obtainable by the processes as described above.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Example 1: Placebo Active Agent Layer

Formulation

The formulation of coating composition A is summarized in Table 1 below. The formulation is based on weight percent, as also indicated in Table 1. Composition A is an active agent-free placebo composition used for evaluating the adhesiveness and can be used as a base composition for incorporating an active agent for potential active agent layer coating compositions.

TABLE 1

| Substance | Composition A Amount [wt-%] |
|---|---|
| PVA 40-88 | 6.64 |
| NaCMC 7MF EP* | 5.63 |
| Glycerol | 3.24 |
| Titan dioxide | 0.68 |
| Klucel GF | 1.80 |
| Water | 82.00 |

*NaCMC 7LP EP is a sodium carboxymethyl cellulose with a degree of substitution of 0.7, a weight average molecular weight of 90,500 and a viscosity of 25-50 mPa · s.

Preparation of Coating Composition (Placebo Active Agent Layer)

Coating composition A was prepared by combining all components of the formulation listed above in Table 1 using standard equipment, e.g., laboratory stirrers and glass beakers, and standard procedures known to the person skilled in the art.

Preparation of Placebo Active Agent Layer

A placebo active agent layer was prepared by coating and drying composition A on a release liner. Coating and drying of the coating composition was carried out using standard equipment such as coating box or coating knife for casting and drying cabinets for drying, by standard procedures known to the person skilled in the art. The coating thickness was adjusted to afford an area weight of 150 g/m$^2$.

Example 2: Backing Layer

Preparation of Coating Composition (Backing Layer)

Backing layer coating compositions were prepared by combining all components of the backing layer for each of the formulations B1 to B6 listed below in Table 2 in the respective solvent to provide a coating composition with a solids content of about 15% by weight using standard equipment, e.g., laboratory stirrers and glass beakers, and standard procedures known to the person skilled in the art. The solvent used was ethanol for formulation B1 and a solution of ethanol and acetone (80:20 v/v) for formulations B2 to B6.

Preparation of Backing Layers

Backing layers B1 to B6 were prepared by coating and drying each of the backing layer compositions on a release liner. Coating and drying of the coating composition was carried out using standard equipment such as coating box or coating knife for casting and drying cabinets for drying, by standard procedures known to the person skilled in the art. The coating thickness was adjusted to afford an area weight of 50 g/m$^2$.

The formulations of the obtained backing layers B1 to B6 are summarized in Table 2 below. The formulations are based on weight percent, as also indicated in Table 2.

TABLE 2

| | Backing layer/Amount [wt-%] | | | | | |
|---|---|---|---|---|---|---|
| Substance | B1 | B2 | B3 | B4 | B5 | B6 |
| Ethyl cellulose N50NF | 89.90 | 74.90 | 69.90 | 64.90 | 59.90 | 59.90 |
| Kollidon SR | — | 15.00 | 20.00 | 25.00 | 30.00 | 30.00 |
| Glycerin | 10.00 | 10.00 | 10.00 | 10.00 | 10.00 | — |
| Triacetin | — | — | — | — | — | 10.00 |
| Colorant Brilliant Blue | 0.10 | 0.10 | 0.10 | 0.10 | 0.10 | 0.10 |

Example 3: Adhesive Layer

Preparation of Coating Compositions (Adhesive Layer)

Adhesive layer coating compositions were prepared by combining all components of the adhesive layer for each of reference formulation R1 as well as formulations C1 to C20 listed below in Tables 3 and 4 in a sufficient amount of solvent (e.g., in an amount to obtain a coating composition with solids content of about 45-55% by weight) using standard equipment, e.g., laboratory stirrers and glass beakers, and standard procedures known to the person skilled in the art.

Preparation of Bi-Layer Laminates

Bi-layer laminates were prepared by coating and drying the adhesive layer coating compositions on top of the dried backing layers obtained in Example 2 to obtain an adhesive layer/backing layer bi-layer laminate on a release liner. Coating and drying of the coating composition was carried out using standard equipment such as coating box or coating knife for casting and drying cabinets for drying, by standard procedures known to the person skilled in the art.

Each of the coating compositions R1 and C1 to C20 were coated on the backing layer B1. In addition, coating compositions C13, C15 and C18 were used to prepare bi-layer laminates with backing layers B2 to B5 each, and coating composition C13 was used to prepare a bi-layer laminate with backing layer B6. The coating thicknesses were adjusted to afford an area weight of 60 g/m$^2$ for the adhesive layer.

Formulation and Evaluation of Adhesive Layers

Haptic evaluation of the adhesive layer was conducted qualitatively by probing the surface of the obtained bi-layer laminate with a finger, applying moderate pressure. The result of the evaluation as well as the formulations of adhesive layers R1 and C1 to C20 are summarized in Table 3 (reference adhesive layer R1) and Table 4 (adhesive formulations C1 to C20) below. The formulations are based on weight percent, as also indicated in Tables 3 and 4.

TABLE 3

| Formulation | Kollidon VA64 [wt-%] | Glycerin [wt-%] | Solvent | Evaluation |
|---|---|---|---|---|
| R1 | 80 | 20 | Ethanol | Sticky |

TABLE 4

| Formulation | Kollidon SR [wt-%] | Glycerin [wt-%] | Further film-former [wt-%] | Solvent | Evaluation |
|---|---|---|---|---|---|
| C1 | 80 | 20 | / | EtOH | Slightly sticky |
| C2 | 70 | 30 | / | | Slightly sticky |
| C3 | 90 | 10 | / | | Not sticky |
| C4 | 85 | 15 | / | | Not sticky |
| C5 | 80 | 20 | / | EtOAc | Not sticky |
| C6 | 80 | 20 | / | Ace | Not sticky |
| C7 | 85 | 15 | / | | Not sticky |
| C8 | 70 | 30 | / | | Not sticky |
| C9 | 60 | 40 | / | | Not sticky |
| C10 | 80 | 20 | / | EtOAc/Ace 67/33 | Not sticky |
| C11 | 80 | 20 | / | EtOAc/Ace 50/50 | Not sticky |
| C12 | 80 | 15 | EC 5 | Ace | Not sticky |
| C13 | 80 | 15 | EC 5 | Ace/EtOH 90/10 | Not sticky |
| C14 | 80 | 15 | HPC 5 | Ace | Not sticky |
| C15 | 80 | 15 | HPC 5 | Ace/EtOH 75/15 | Not sticky |
| C16 | 75 | 15 | HPC 10 | Ace/EtOH 80/20 | Not sticky |
| C17 | 80 | 15 | HPC 5 | Ace/EtOH 65/35 | Not sticky |
| C18 | 75 | 15 | EC 5 HPC 5 | Ace/EtOH 65/35 | Not sticky |
| C19 | 65 | 15 | EC 20 | Ace/EtOH 80/20 | Not sticky |
| C20 | 75 | 15 | EC 10 | Ace/EtOH 80/20 | Not sticky |

EC = ethyl cellulose N50NF,
HPC = Klucel EF,
EtOH = ethanol,
EtOAc = ethyl acetate,
Ace = acetone In comparison to the reference adhesive layer R1 based on Kollidon VA64, adhesive layers C1 to C20 based on Kollidon SR exhibited a reduced tack (see Table 3 versus Table 4 above).

Example 4: Placebo Oromucosal Therapeutic Systems

Active agent-free placebo oromucosal therapeutic systems were manufactured and used for evaluating the adhesion provided by the adhesive layer, as described in the following.

Preparation of Oromucosal Therapeutic Systems

Oromucosal therapeutic systems were prepared by laminating the adhesive layer/backing layer bi-layer laminates obtained in Example 3 with the placebo active agent layer obtained in Example 1 (with the laminates and placebo layer arranged so that the adhesive layer faces the placebo layer). Lamination was carried out using standard equipment such as a conventional laminating station, by standard procedures known to the person skilled in the art. The release liner covering the backing layer was removed and individual oromucosal therapeutic systems 6 $cm^2$ (20 mm*30 mm) in size were punched out.

Formulation and Evaluation of Oromucosal Therapeutic Systems

The individual oromucosal therapeutic systems were evaluated as outlined in the following.

Dissolution Behaviour

A sample of an oromucosal therapeutic system based on formulations A/R1/B1 (active agent layer/adhesive layer/backing layer) was provided in a small aluminum bowl containing 3 mL water or saliva. Disintegration and separation of the layers was observed up to 60 min. In this reference system A/R1/B1 using an adhesive layer based on Kollidon VA64, the layers already separated after 30 minutes in water and also in saliva. However, by using an adhesive layer based on Kollidon SR (e.g., formulation C1), a hardly water-soluble active agent layer and a water insoluble backing layer, an oromucosal therapeutic system could be manufactured, which remained stable for 60 minutes in human saliva. Using systems based on formulations A, B2 and C14, retention times of at least 60 minutes in human saliva could be attained without showing signs of separation of the layers.

Adhesion

A first overall impression of adhesive properties provided by the adhesive layer, i.e., whether the laminate shows any sign of obviously improper adhesion, was evaluated immediately after laminating and preparing individual oromucosal therapeutic systems as outlined above.

Lateral Movement of the Layers

In order to assess lateral movement between the layers, the obtained individual systems were positioned between the thumb and the middle finger. Thumb and middle fingers were then slid against each other under moderate pressure several times to assess the ability of the systems to resist against the shear force applied. It was observed whether the layers could be moved laterally.

Separation of the Layers

In order to assess the risk of layer separation, the obtained oromucosal therapeutic systems were subjected to attempts of manually pulling apart the backing layer from the placebo active agent layer. A quantitative assessment using a mechanical device did not appear possible.

To pull apart the layers, it was necessary to actively bend a corner of the system to create a folded "peel tab" for all systems. With the aid of such a peel tab, separation of the layers required little to moderate pull force, and it was observed how easy the layers could be separated. In some cases, the layers could not be separated without the layers tearing apart.

The results of the evaluation are summarized in Tables 5 to 7 below.

TABLE 5

| Active agent layer | Adhesive layer | Backing layer | Adhesion between layers | Lateral movement of the layers | Separation of the layers |
|---|---|---|---|---|---|
| A | C1 | B1 | good | none | easy |
| | C2 | | acceptable | possible | very easy |
| | C3 | | good | possible | very easy |
| | C4 | | good | possible | very easy |
| | C5 | | good | none | easy |
| | C6 | | good | none | easy |
| | C7 | | good | none | easy |
| | C8 | | good | none | easy |

TABLE 5-continued

| Active agent layer | Adhesive layer | Backing layer | Adhesion between layers | Lateral movement of the layers | Separation of the layers |
|---|---|---|---|---|---|
| | C9 | | good | none | easy |
| | C10 | | good | none | very easy |
| | C11 | | good | none | very easy |
| | C12 | | good | none | easy |
| | C13 | | good | none | easy |
| | C14 | | good | none | possible |
| | C15 | | good | none | possible |
| | C16 | | good | none | possible |
| | C17 | | good | none | possible |
| | C18 | | good | none | possible |
| | C19 | | good | none | easy |
| | C20 | | good | none | easy |

Table 5 shows the results obtained for the systems based on backing layer B1 and each of reference adhesive layer R1 and adhesive layers C1 to C20 (systems A/R1/B1 and A/C1/B1~A/C20/B1). Adhesive layers C2 to C11 are variants of adhesive layer C1 using different solvents, area weights or amounts of plasticizer (see Table 4 above). The water solubility of the adhesive layer does not change by these modifications.

Systems based on adhesive layer formulations C1 to C11 resulted mostly in a good adhesion and the laminates showed high stability against shear forces except those based on formulations C2 to C4 obtained with only ethanol as solvent. The results of systems based on adhesive layer formulations C14 to C17 with hydroxypropyl cellulose (Klucel EF) show that an additional improvement could be achieved by incorporating a low amount of the film-forming polymer used in the active agent layer into the adhesive layer.

Incorporation of ethyl cellulose into the adhesive layer resulted in a slight improvement of adhesion. However, adhesive layers with a higher proportion of ethyl cellulose become brittle and stiffer so that adhesion is reduced (systems A/C19/B1 and A/C20/B1), thus, it is preferable to keep the amount of ethyl cellulose in the adhesive layer below 10 wt-%.

As outlined above, it was impossible to manually separate the layers without creating a peel tab aid. It is assumed that no layer separation will occur when oromucosal therapeutic systems based on formulations A, B1 as well as C1, C5 to C9 and C12 to C18 are administered correctly and without mis- or abuse attempts.

TABLE 6

| Active agent layer | Adhesive layer | Backing layer | Adhesion between layers | Lateral movement of the layers | Separation of the layers |
|---|---|---|---|---|---|
| A | C13 | B2 | good | none | difficult |
| | C15 | | good | none | difficult |
| | C18 | | good | none | possible |
| A | C13 | B3 | good | none | difficult |
| | C15 | | good | none | difficult |
| | C18 | | good | none | possible |
| A | C13 | B4 | good | none | difficult |
| | C15 | | good | none | difficult |
| | C18 | | good | none | possible |
| A | C13 | B5 | good | none | difficult |
| | C15 | | good | none | difficult |
| | C18 | | good | none | possible |

Table 6 shows the results obtained for the systems based on backing layers B2 to B5 and adhesive layers C13, C15 and C18. These systems show that the best results in terms of backing layer/adhesive layer combinations could be achieved by adding Kollidon SR into the backing layer (formulations B2 to B5). The amount of Kollidon SR can be increased up to 60 wt-% without adverse effects on, e.g., adhesive properties or manufacturing. As Kollidon SR is not water soluble, the water solubility of the backing layer does not change between backing layers B1 to B5. The combination of backing layers B2 to B5 with adhesive layers C13 or C15 created the strongest bond between the layers. It is assumed that during coating of the adhesive layer coating composition on the backing layer, the backing layer is slightly dissolved at its surface, which allows for an interaction of the Kollidon SR chains from the adhesive layer with the Kollidon SR chains of the backing layer resulting in a stronger bond.

By using an adhesive layer based on formulation C18, which in addition to Kollidon SR also comprises ethyl cellulose and hydroxypropyl cellulose (Klucel EF), the adhesion between backing layers B2 to B5 and active agent layer A could not be improved. To the contrary, such a system A/C18/B2 showed even a reduced adhesion when compared to systems based on adhesive layers C13 or C15 (A/C13/B2 and A/C15/B2).

For all systems evaluated above (see Table 6), it was impossible to manually separate the layers without creating a peel tab aid. It is assumed that no layer separation will occur when these oromucosal therapeutic systems are administered correctly and without mis- or abuse attempts.

TABLE 7

| Active agent layer | Adhesive layer | Backing layer | Adhesion between layers | Lateral movement of the layers | Separation of the layers |
|---|---|---|---|---|---|
| A | C13 | B6 | good | none | difficult |

Table 7 shows the results obtained for a system based on backing layer B6 and adhesive layer C13. Especially preferred is a combination of formulations C13 and B6. The system A/C13/B6 showed the highest resistance against manual separation after 60 minutes of exposure to water or human saliva, and like the other systems based on backing layers B2 to B5, it was impossible to manually separate the layers of system A/C13/B6 without creating a peel tab aid. It is assumed that no layer separation will occur when this oromucosal therapeutic system is administered correctly and without mis- or abuse attempts.

The excellent adhesion is assumed to be based on the high amount of Kollidon SR and the use of triacetin as plasticizer. Both components increase the flexibility of the backing layer, which can, thus, better adapt to the adhesive layer. Furthermore, triacetin exhibits a lower water solubility than glycerin. Laminates based on backing layer B2 and adhesive layer C13 show an increased dissolution of the water-soluble glycerin. By losing the plasticizer, the adhesive layer becomes stiff and the contact area between adhesive and backing layer is reduced, resulting in a reduction of adhesion between the two layers. Triacetin has a lower water solubility than glycerin and, thus, will not dissolve out from the backing layer. The backing layer remains flexible and the adhesion between the layers will not be reduced.

The invention claimed is:

1. An oromucosal therapeutic system for the oromucosal administration of an active agent comprising a mucoadhesive layer structure comprising A) a backing layer comprising a first film-forming polymer, B) an adhesive layer comprising a laminating adhesive; and a first plasticizer, and C) an active agent-containing layer comprising a second film-forming polymer, wherein the laminating adhesive is a mixture comprising polyvinylpyrrolidone and polyvinylacetate, wherein the polyvinylacetate has a molecular weight of from 400,000 to 500,000, and the first plasticizer is selected from the group consisting of mono-, di-, oligo- and polysaccharides and derivatives thereof, triacetin, triethyl citrate, tributyl citrate, propylene glycol, glycerin, medium chain triglycerides and any mixture thereof.

2. The oromucosal therapeutic system according to claim 1, wherein the adhesive layer is adjacent to the active agent-containing layer on a first side and to the backing layer on a second side.

3. The oromucosal therapeutic system according to claim 1, wherein the active agent-containing layer is a mucosa-contacting layer.

4. The oromucosal therapeutic system according to claim 1, wherein the laminating adhesive is a mixture consisting essentially of polyvinylpyrrolidone and polyvinylacetate.

5. The oromucosal therapeutic system according to claim 1, wherein the laminating adhesive is a mixture comprising from 10 to 30 wt-%, from 15 to 25 wt-%, or about 19 wt-% polyvinylpyrrolidone, from 70 to 90 wt-%, from 75 to 85 wt-%, or about 80 wt-% polyvinylacetate, and about 1 wt-% of one or more stabilizers, optionally wherein said mixture has a K-value of from 60 to 68 or a glass transition temperature Tg of about 35° C.

6. The oromucosal therapeutic system according to claim 1, wherein the polyvinylpyrrolidone is a soluble polyvinylpyrrolidone.

7. The oromucosal therapeutic system according to claim 1, wherein the polyvinylacetate has a molecular weight of about 450,000.

8. The oromucosal therapeutic system according to claim 1, wherein the adhesive layer further comprises a film-forming polymer.

9. The oromucosal therapeutic system according to claim 1, wherein the adhesive layer comprises from 50 to 90 wt-%, or from 60 to 85 wt-% of the laminating adhesive, from 10 to 45 wt-%, or about 15 wt-% of the first plasticizer, and from 0 to 10 wt-%, or about 5 wt-% of the first or second film-forming polymer each.

10. The oromucosal therapeutic system according to claim 1, wherein the backing layer is water-insoluble and further comprises a second plasticizer in an amount of 5 to 20 wt-%, or about 10 wt-% of the backing layer, wherein the second plasticizer is selected from the group consisting of mono-, di-, oligo- and polysaccharides and derivatives thereof and any mixture thereof, or a laminating adhesive aid in an amount of up to 60 wt-%, or from 10 to 35 wt-% of the backing layer, wherein the laminating adhesive aid is a mixture consisting essentially of polyvinylpyrrolidone and polyvinylacetate.

11. The oromucosal therapeutic system according to claim 1, wherein the first film-forming polymer is selected from the group consisting of ethyl cellulose, a copolymer based on dimethylaminoethyl methacrylate, butyl methacrylate and methyl methacrylate, and any mixtures thereof, or the first film-forming polymer is ethyl cellulose with a viscosity as measured as a 5% solution at 25° C. in 80:20 toluene: ethanol by weight in accordance with ASTM D914 of from 30 to 60 mPa·s, or from 40 to 52 mPa·s, or a substitution of ethoxyl groups of 48.0 to 49.5% as measured in accordance with ASTM D914, or a moisture content of 3% by weight or less, in an amount of from 55 to 95 wt-%, or about 60 wt-% of the backing layer.

12. The oromucosal therapeutic system according to claim 1, wherein the second film-forming polymer is selected from the group consisting of ethyl cellulose, hydroxypropyl cellulose, carboxymethyl cellulose sodium, polyvinyl alcohol, hydroxypropyl methyl cellulose, polyvinylpyrrolidone, polyethylene oxide, polyethylene glycol, hydroxyethyl cellulose, methacrylic acid-methyl methacrylate copolymer (1:1) in neutralized form, and any mixture thereof, optionally wherein the second film-forming polymer is a mixture of polymers in an amount of 5 to 50 wt-%, or 10 to 40 wt-% of the active agent-containing layer per polymer.

13. The oromucosal therapeutic system according to claim 1, wherein the adhesive layer is obtainable by combining the laminating adhesive, the first plasticizer and optionally a film-forming polymer and further optional excipients in a solvent selected from ethanol, ethyl acetate, acetone and any mixture thereof, casting the obtained composition on the backing layer or one of the other layers of the mucoadhesive layer structure to obtain a casted film, and drying the casted film.

14. A method of treating or preventing diseases and medical conditions in a human patient, comprising administering to the patient the oromucosal therapeutic system according to claim 1.

15. The oromucosal therapeutic system for the oromucosal administration of an active agent according to claim 1, comprising a mucoadhesive layer structure consisting of A) a backing layer comprising from 55 to 95 wt-%, or about 60 wt-% of ethyl cellulose, from 5 to 20 wt-%, or about 10 wt-% triacetin, from 10 to 35 wt-%, or about 30 wt-% of a mixture consisting of about 19 wt-% polyvinylpyrrolidone, about 80 wt-% polyvinylacetate, about 0.8 wt-% sodium lauryl sulfate and about 0.2 wt-% of silica, B) an adhesive layer adjacent to the active agent-containing layer on a first side and to the backing layer on a second side, comprising from 70 to 90 wt-%, or about 80 wt-% of a mixture consisting of,
about 19 wt-% polyvinylpyrrolidone,
about 80 wt-% polyvinylacetate,
about 0.8 wt-% sodium lauryl sulfate and
about 0.2 wt-% of silica,
from 10 to 30 wt-%, or about 15% of glycerin, and
from 0 to 10 wt-%, or about 5 wt-% of a film-forming polymer selected from the group consisting of ethyl cellulose, hydroxypropyl cellulose, carboxymethyl cellulose sodium, polyvinyl alcohol, hydroxypropyl methyl cellulose, polyvinylpyrrolidone, polyethylene oxide, polyethylene glycol, hydroxyethyl cellulose, methacrylic acid-methyl methacrylate copolymer (1:1) in neutralized form, and any mixture thereof, and C) an active agent-containing layer comprising
an active agent, and
a second film-forming polymer selected from the group consisting of ethyl cellulose, hydroxypropyl cellulose, carboxymethyl cellulose sodium, polyvinylalcohol, hydroxypropyl methyl cellulose, polyvinylpyrrolidone, polyethylene oxide, polyethylene glycol, hydroxyethyl cellulose, methacrylic acid-methyl methacrylate copolymer (1:1) in neutralized form, and any mixture thereof.

16. The oromucosal therapeutic system according to claim 6, wherein
the soluble polyvinylpyrrolidone is a polyvinylpyrrolidone having a K-Value of from 28 to 32, or a molecular weight of from 44,000 to 54,000.

17. The oromucosal therapeutic system according to claim 12, wherein
the second film-forming polymer is a mixture of polyvinyl alcohol, carboxymethyl cellulose sodium and hydroxypropyl cellulose, in a total amount of 70 to 90 wt-%, or about 80 wt-% of the active agent-containing layer.

* * * * *